United States Patent [19]
Bennani et al.

[11] Patent Number: 5,514,821
[45] Date of Patent: May 7, 1996

[54] RING-LABELED RETINOIDS AND INTERMEDIATES, AND METHODS FOR THEIR SYNTHESIS AND USE

[75] Inventors: Youssef L. Bennani, La Jolla; Marcus F. Boehm, San Diego, both of Calif.

[73] Assignee: Ligand Pharmaceuticals Incorporated, San Diego, Calif.

[21] Appl. No.: 250,368

[22] Filed: May 27, 1994

[51] Int. Cl.$^6$ .................................................. C07C 57/26
[52] U.S. Cl. ........................................ 554/221; 423/647.7
[58] Field of Search .................. 584/221; 423/647.7; 424/1.1

[56] References Cited

U.S. PATENT DOCUMENTS 5,196,577  3/1993  Shroot et al. ............................ 562/490

FOREIGN PATENT DOCUMENTS 3142975  5/1983  Germany.

OTHER PUBLICATIONS

Kaegi, H. and J. DeGraw, "Preparation of All Trans–Retinyl–11–$^3$H Acetate," 18 *Journal of Labelled Compounds and Radiopharmaceuticals* 1099 (1981).

Chien, P.; Sung, M; and Bailey, D., "Synthesis of trans–[11–$^3$H]–Retinoic Acid and Its 5,6–Epoxide," 17 *Journal of Labelled Compounds and Radiopharmaceuticals*, 759 (1980).

Chien, P. and Sung, M., "Synthesis of 13–cis–(11–$^3$H)–Retinoic Acid," 16 *Journal of Labelled Compounds and Radiopharmaceuticals*, 791 (1979).

Rhee, S., DeGraw, J., and Kaegi, H., "Synthesis of a New Class of Retinoid, $^3$H–Labeled TTNPB,$^1$ with a High Specific Activity," 22 *Journal of Labelled Compounds and Radiopharmaceuticals*, 843 (1985).

Dawson, M.; Hobbs, P.; Cameron,J.; and Rhee, S., "Preparation of 9–cis–Retinoic Acid [11,12–H(N)] by Photochemical Isomerization," 33 *Journal of Labelled Compounds and Radiopharmaceuticals*, 245 (1993).

Cainelli, G.; Cardillo, Giuliana; and Orena, Mario, "Synthesis of Compounds Containing the Isoprene Unit; a Stereospecific Synthesis of β–Ionilideneactic Acid and Dehydro–β–ionilideneactic Acid, a Key Intermediate to Abscisic Acid," *J.C.S. Perkin I.* 1597 (1979).

Kaegi, H., "Synthesis of Retinoids Labeled with Radioisotopes," Ch. 3, *The Retinoids*, vol. 1, pp.147–179 (1984).

Colwell, W., SooHoo, C., and DeGraw, J., "Synthesis of Rin 14C–Methyl Labeled Retinyl Acetate," 16 *Journal of Labelled Compounds and Radiopharmaceuticals*, pp. 551–560 (1979).

Dawson, M.; Hobbs, P., Chan, R.; and Chao, W., "Retinoic Acid Analogues with Ring Modifications. Synthesis and Pharmacological Activity," 24 *J. Med. Chem.*, pp. 1214–1223 (1981).

Heyman, R.; Mangelsdorf; Dyck, J.; Stein, R.; Eichele, G.; Evans, R.; and Thaller, C., "9–Cis–Retinoic Acid is a High Affinity Ligand for the Retinoid X Receptor," 68 *Cell*, 397 (1992).

*Primary Examiner*—José G. Dees
*Assistant Examiner*—Deborah D. Carr

[57] ABSTRACT

Methods for the synthesis of dideuterium and/or ditritium ring-labeled retinoids and intermediates, and their use in the discovery of Retinoid X Receptor ligands are provided. In addition, dideuterium and/or ditritium ring-labeled retinoids and novel intermediates, as well as methods for their use in ligand binding and mass spectral studies are also provided.

9 Claims, 2 Drawing Sheets

RING-LABELED RETINOIDS AND INTERMEDIATES, AND METHODS FOR THEIR SYNTHESIS AND USE

FIELD OF THE INVENTION

The present invention relates to the synthesis of ring-labeled compounds, and in particular to the synthesis of ring-labeled retinoids and their intermediates. The present invention also relates to ring-labeled retinoids and their intermediates, as well a to the use of such ring-labeled retinoids and related compounds in ligand competition binding analyses and mass spectral studies.

BACKGROUND OF THE INVENTION

The role of retinoids such as all-trans retinoic acid (ATRA), 13-cis retinoic acid (13-cis RA) and synthetic retinoic acid (RA) analogs in mediating cell growth and differentiation has generated interest in their pharmacological utility for controlling the treatment of dermatological diseases, such as psoriasis and acne, as well as oncological applications such as chemotherapy and chemoprevention. Significant advances in elucidating the molecular basis of retinoid action now offer the potential for designing retinoic acid compounds with improved therapeutic indices.

To date, several receptors for retinoic acid have been identified. These receptors are members of a superfamily of intracellular receptors which function as ligand dependent transcription factors. At present, these receptors have been classified into two subfamilies, the retinoic acid receptors (RARs) and retinoid X receptors (RXRs). The classification of these subfamilies is based primarily on differences in amino acid structure, responsiveness to different naturally occurring and synthetic retinoids, and ability to modulate expression of different target genes. Each RAR and RXR subfamily has three distinct isoforms designated RARα, RARβ and RARγ, and RXRα, RXRβ and RXRγ. The discovery of multiple retinoid receptors raises questions of the functional properties of the distinct subfamilies and their isoforms.

Recently, it has been discovered that 9-cis RA is capable of binding to and modulating gene expression via the RARs and RXRs. See Heyman et al., *Cell*, 68:397 (1992). The discovery of this property of 9-cis RA has led to further investigation into the biochemical properties of the RARs and RXRs with naturally occurring retinoic acid as well as with synthetic retinoids.

One technique for determining the affinity of retinoic acid and synthetic retinoids to RARs and associated proteins is to employ a competitive ligand binding assay using radiolabeled compounds showing RAR activity. See e.g., U.S. Pat. No. 5,196,577. These ligand binding studies require substantial quantities, i.e. greater than 50 millicuries, of a high specific activity radiolabeled compound. However, conventional syntheses of radiolabeled retinoids such as ATRA, using e.g. photoisomerization, is costly and generally cannot yield sufficient quantities of the radiolabeled retinoid to effectively conduct ligand binding studies. In particular, conventional syntheses cannot provide sufficient quantities of preferred radiolabeled retinoid stereoisomers, such as 9-cis RA, 13-cis RA and 9,13-dicis RA. See also, M. I. Dawson et al., *J. Labeled Compd. Radiopharm.*, 33:245 (1993) (photoizomerization to yield μCi quantities of tritium-labeled 9-cis retinoic acid) and H. H. Kaegi et al., *J. Labeled Compd. Radiopharm.*, 18:1099 (1981). Furthermore, to date, no radiolabeled compounds have been identified that show activity on RXRs, as well as RARs.

SUMMARY OF THE INVENTION

The present invention provides methods for the synthesis of deuterium and tritium ring-labeled retinoid stereoisomers. In a preferred aspect, the methods of the present invention provide for the synthesis of ditritium ting-labeled 9-cis retinoic acid having a specific activity of at least 15 Ci/mmol, and more preferably at least 25 Ci/mmol, and most preferably, at least 40 Ci/mmol. Importantly, the methods of the present invention provide ring-labeled retinoids, with two deuterium and or tritium atoms at ideal positions in the ring system of the molecule, namely at carbons 2 and 3 or at carbons 3 and 4, all of which show low susceptibility to metabolic oxidation in vitro or in vivo. In this regard, it is particularly preferred to position such deuterium or tritium labels at carbons 2 and 3 (positions 2 and 3), which are apparently the positions least subject to metabolic oxidation in such retinoid compounds.

A further advantage of deuterium or tritium ting-labeled 9-cis retinoic acid over other labeled retinoids is that they bind to all the known RARs and RXRs with approximately equal nanomolar affinities and hence, are a useful probe for determining binding of synthetic retinoids at each of these receptors or in mass spectral studies on the metabolites of such compounds. Thus, the present invention also provides methods for discovering RXR active and RAR and RXR selective compounds using radiolabeled retinoids in competitive ligand binding assays. In particular, tritium-labeled 9-cis RA can be used to discover novel ligands which show RXR activity and selectivity.

In particular, the present invention provides deuterium and/or tritium ring-labeled retinoids, wherein the ring component of the retinoid is substituted with deuterium or tritium at carbons 2 and 3 or carbons 3 and 4. Preferably, such ring-labeled retinoids are labeled with an essentially carrier free tritium gas, thereby yielding a ditritium ring-labeled retinoid having a specific activity of at least 15 Ci/mmol, and more preferably at least 25 Ci/mmol, and most preferably of at least 40 Ci/mmol. Even more preferably, such ditritium ring-labeled retinoids comprise ditritium ting-labeled 9-cis retinoids. As used herein, a substantially carrier-free tritium gas" refers to a radioactive (tritiated) gaseous reducing agent comprising all, or essentially all, tritide atoms, with essentially no hydride (hydrogen) atoms.

The present invention also provides a method for producing a ring-labeled retinoid comprising (a) isomerizing a 2,4-cyclohexadiene-1-carboxaldehyde to form a 1,4-cyclohexadiene-1-carboxaldehyde, (b) condensing the 1,4-cyclohexadiene- 1-carboxaldehyde with an acrylate anion to form a lactone, (c) reducing the lactone to the corresponding lactol and ring-opening the lactol to form an aldehyde, (d) condensing the aldehyde with a carbanion equivalent formed by the addition of a base to a phosphonate or phosphonium salt to form a first reaction product comprising a mixture of retinoid ester stereoisomers, and (e) selectively reducing the first reaction product with metal-catalyzed deuterium or tritium to form a second reaction product comprising a mixture of ring-labeled retinoid ester stereoisomers, wherein 9–10, 11–12 and 13–14 olefin bonds are in either the trans or cis configuration. Further, the second reaction product can be hydrolyzed with an aqueous methanolic hydroxide to form a mixture of ring-labeled retinoic acid stereoisomers, followed by purification and isolation of the individual ring-labeled retinoid stereoisomers. Importantly, these methods place at least two deuterium and/or tritium atoms on the six-membered ring of the retinoid compounds, thereby facilitating the Indentification of ring-containing metabolites in animal metabolism studies.

Furthermore, the present invention also provides ditritium ring-labeled 9-cis retinoids, as well as non-labeled and labeled intermediates that are usable in the preparation of such ditritium ring-labeled 9-cis retinoids.

In addition, the present invention provides a method of producing a 1,4-cyclohexadiene-1-carboxaldehyde comprising isomerizing a 2,4-cyclohexadiene-1-carboxaldehyde in the presence of a catalytic amount of base to yield a 1,4-cyclohexadiene-1-carboxaldehyde.

The present invention further provides methods of identifying retinoid X receptor ligands utilizing the ring-labeled compounds of the present invention in competitive ligand binding studies, as well as use of the ring-labeled compounds of the present invention in mass spectral metabolism and as mass spectral standards for use in quantifying the amount of a non-labeled compound in a biological sample.

These and various other advantages and features of novelty which characterize the invention are pointed out with particularity in the claims annexed hereto and forming a part hereof. However, for a better understanding of the invention, its advantages, and objects obtained by its use, reference should be had to the accompanying drawings and descriptive matter, in which there is illustrated and described preferred embodiments of the invention.

BRIEF DESCRIPTION OF THE DRAWINGS

The invention may be further illustrated by reference to the accompanying Drawings wherein.

DETAILED DESCRIPTION OF EMBODIMENTS OF THE INVENTION

In accordance with a first aspect of the present invention, we have developed dideuterium and/or ditritium ring-labeled retinoids of the formula:

OR

-continued wherein $R^1$, $R^2$, $R^3$, $R^4$ and $R^5$ each can independently represent hydrogen or a lower straight chain or branched alkyl, aryl, heteroaryl or aralkyl having 1–12 carbon atoms;

$R^7$ represents hydrogen or a pharmaceutically acceptable salt;

n=2 or 3; and the dashed lines in the structures between carbons 9–10, 11–12 and 13–14 depict olefin bonds that are in either the trans or cis configuration.

As used in this disclosure, pharmaceutically acceptable salts include, but are not limited to, pyridine, ammonium, piperazine, diethylamine, nicotinamide, sodium, potassium, calcium, magnesium, zinc, lithium, methylamino, triethylamino, dimethylamino, and tris(hydoxymethyl)aminomethane. Additional pharmaceutically acceptable salts are known to those skilled in the art.

These retinoids preferably include essentially pure deuterium and/or tritium at ring carbons 2 and 3 or 3 and 4, as a result of being synthesized with a substantially carder-free deuterium or tritium gas. Accordingly, when labeled with substantially carrier-free tritium gas, these retinoids display a specific activity of at least 15 Ci/mmol, more preferably, at least 25 Ci/mmol, and most preferably, at least 40 Ci/mmol. In fact, the ditritium, ring-labeled retinoids of the present invention display a specific activity of as high as 58 Ci/mmol.

In a second aspect of the present invention, we have developed several methods to synthesize deuterium and tritium ting-labeled retinoids. The sequence of steps for two general schemes of these methods are shown below.

SCHEME 1

SCHEME 1 -continued

SCHEME 2 wherein $R^1$, $R^2$, $R^3$, $R^4$ and $R^5$ each can independently represent hydrogen or a lower straight chain or branched alkyl, aryl, heteroaryl or aralkyl having 1–12 carbon atoms;

$R^6$ represents a lower straight chain or branched alkyl having 1–5 carbon atoms;

$R^7$ represents hydrogen or a pharmaceutically acceptable salt;

n=2 or 3; and the dashed lines in the structures between carbons 9–10, 11–12 and 13–14 depict olefin bonds that are in either the trans or cis configuration.

It will be understood by those skilled in the art that certain modifications can be made to the above-described methods that remain within the scope to the present invention. For example, a dihydro-retinoic ester such as compound VIII in Scheme 1 or compound XII in Scheme 2 can be reduced with tritium gas under metal-catalyzed conditions to give the tritiated products IX and XIII. The advantage of this method is that a remote olefin can be selectively reduced in the presence of other olefins. Additionally, two tritium atoms can be incorporated into the ring of each molecule, thereby increasing the specific activity of the retinoid, and allowing for the discovery of ring-metabolites in animal metabolism studies. The catalyst used in such methodologies may be Pd/C, Pt/C, Rh/C, Wilkinson's (RhCl(PPh$_3$)$_3$), or any other appropriate catalyst known to those skilled in the art.

Scheme 1

The process in Scheme 1 begins with the synthesis of the 2,4-cyclohexadiene-1-carboxaldehyde IV precursor. Specifically, β-Keto esters of type I, such as ethyl acetoacetate, are condensed with a ketone, such as acetone, in the presence of acetic anhydride under zinc chloride catalysis to give ketone compounds of type II, such as ethyl isopropylidene acetoacetate. These type II ketone compounds are then reacted with allyl phosphorylide in a Michael-Wittig type of reaction to give a cyclic ester III, such as ethyl 2,6,6-trimethyl 2,4-cyclohexadiene-1-carboxylate. See e.g., Wüest et al., *Helv. Chim. Acta,* 54:1767 (1971), the disclosure of which is herein incorporated by reference. Lithium aluminum hydride reduction, followed by Swern oxidation yields the corresponding 2,4-cyclohexadiene-1-carboxaldehyde precursor IV, such as 2,6,6-trimethyl-2,4-cyclohexadien-1-carboxaldehyde.

The unique aspects of Scheme 1 begin with the isomerization of the 2,4-cyclohexadiene-1-carboxaldehyde precursor IV in the presence of a catalytic amount of base, such as 1,8-diazabicyclo[5.4.0]undec7-ene (DBU), to give a 1,4-cyclohexadiene carboxaldehyde V, such as 2,6,6-trimethyl 1,4-cyclohexadiene-1-carboxaldehyde. Thereafter, in the second step, the 1,4-cyclohexadiene-1-carboxaldehyde V is condensed with an acrylate anion, for example, with a lithium anion derived from ethyl dimethyl acrylate, to give a lactone VI, such as 5,6-dihydro-4-methyl-6-(2,6,6-trimethyl-1,4-cyclohexadiene-1-yl)-2H-pyran-2-one.

The third step of the method involves reduction of lactone VI to the corresponding lactol (not shown), such as 5,6-dihydro-4-methyl-6-(2,6,6-trimethyl-1,4-cyclohexadiene-1-yl)-2H-pyran-2-ol, using Dibal (diisobutylaluminum hydride), followed by hydrochloric acid-catalyzed ring-opening to yield an aldehyde VII, such as (2Z,4E)-3-methyl-5-(2,6,6-trimethylcyclohex-1,4-dienyl)-2,4-pentadieneal.

The fourth step of this sequence of Scheme 1 involves the condensation of aldehyde VII with a carbanion equivalent formed by the addition of a base (n-BuLi) to a phosphonate, such as diethyl-3-ethoxycarbonyl-2-methylprop-2-enyl phosphonate, or a phosphonium salt to yield a first reaction product comprising retinoate (retinoid ester) VIII, such as ethyl (2E,4E,6Z,8E)-3,7-dimethyl-9-(2,6,6-trimethylcyclohex-1,4-dienyl)-nona-2,4,6,8-tetraenoate. After condensation, a mixture of one major isomer and at least two minor isomers (<10% of the total) of retinoates VIII is observed. Nonlimiting examples of bases useful in this method of the present invention include sodium hydride (NaH), potassium hydride (KH), n-butyl lithium (n-BuLi), s-butyl lithium (s-BuLi), t-butyl lithium (t-BuLi), and sodium amide (NaNH₂).

The fifth and final step in the process of Scheme 1 involves site selective catalytic reduction of the first reaction product comprising retinoates VIII using a metal catalyst, such as RhCl(PPh₃)₃ (e.g. Wilkinson's catalyst), in the presence of tritium gas, preferably carrier-free tritium gas, to yield a second reaction product comprising retinoid ester IX, such as ethyl (2E,4E,6Z,8E)-4,5-[³H₂]-3,7-dimethyl-9'(2,6,6-trimethylcyclohex-1-enyl)-nona-2,4,6,8-tetraenoate. Thereafter, hydrolysis of second reaction product comprising retinoid esters IX with aqueous methanolic hydroxide (MeOH/KOH) yields ditritium ring-labeled retinoic acid isomers XI. Examples of ditritium ring-labeled retinoid isomers XI include, without limitation, 4,5-[³H₂]-9-cis retinoic acid ((2E,4E,6Z,8E)-4,5-[³H₂]-3,7-dimethyl-9-(2,6,6)-trimethylcyclohex-1-enyl)-nona-2,4,6,8-tetraenoic acid), 4,5-[³H₂]-13-cis retinoic acid ((2Z,4E,6E,8E)-4,5-[³H₂]-3,7-dimethyl-9-(2,6,6-trimethylcyclohex-1-enyl)-nona-2,4,6,8-tetraenoic acid), 4,5-[³H₂]-all-trans retinoic acid ((2E,4E,6E,8E)-4,5-[³H₂]-3,7-dimethyl-9-(2,6,6-trimethylcyclohex-1-enyl)-nona-2,4,6,8-tetraenoic acid), and 4,5-[³H₂]-9,13-dicis retinoic acid ((2Z,4E,6Z,8E)-4,5-[³H₂]-3,7-dimethyl-9-(2,6,6-trimethylcyclohex-1-enyl)-nona-2,4,6,8-tetraenoic acid). After hydrolysis, a desired ditritium ring-labeled stereoisomer XI can be selectively crystallized from the aqueous methanolic hydroxide solution, or alternatively purified by semi preparative reverse-phase (ODS) high performance liquid chromatography (HPLC).

Further, it will be understood by those skilled in the art that the selective reduction in the final step with using a metal catalyst, such as RhCl(PPh₃)₃ (e.g. Wilkinson's catalyst), in the presence of deuterium gas, preferably carrier-free deuterium gas, will yield dideuterium, ring-labeled retinoids (i.e. isotopically labeled retinoids) according to the present invention, including, without limitation, 4,5-[²H₂]-9-cis retinoic acid ((2E,4E,6Z,8E)-4,5-[²H₂]-3,7-dimethyl-9-(2,6,6-trimethylcyclohex-1-enyl)-nona-2,4,6,8-tetraenoic acid), 4,5-[²H₂]-13-cis retinoic acid ((2Z,4E,6E,8E)-4,5-[²H₂]-3,7-dimethyl-9-(2,6,6-trimethylcyclohex-1-enyl)-nona-2,4,6,8-tetraenoic acid), 4,5-[²H₂]-all-trans retinoic acid ((2E,4E,6E,8E)-4,5-[²H₂]-3,7-dimethyl-9-(2,6,6-trimethylcyclohex-1-enyl)-nona-2,4,6,8-tetraenoic acid), and 4,5-[2H₂]-9,13-dicis retinoic acid ((2Z,4E,6Z,8E)-4,5-[²H₂]-3,7-dimethyl-9-(2,6,6-trimethylcyclohex-1-enyl)-nona-2,4,6,8-tetraenoic acid).

Scheme 2

The process in Scheme 2 begins with a modification of the fifth step of Scheme 1. Specifically, a retinoate compound XII (where R¹, R², R³, R⁴ and R⁵ are methyl), which was prepared according to literature references by Cainelli et al., *J. Chem. Soc.,* 1957 (1979) and Schwieter et al., *Helv. Chim. Acta,* 63:528 (1962), the disclosures of which are herein incorporated by reference, is subjected to site selective catalytic reduction of using a metal catalyst, such as RhCl(PPh₃)₃ (e.g. Wilkinson's catalyst), in the presence of tritium gas [or deuterium gas] to yield a reaction product comprising a mixture of labeled retinoid ester XIII, such as ethyl (2E,4E,6Z,8E)-3,4-[³H₂]-3,7-dimethyl-9-(2,6,6-trimethylcyclohex-1-enyl)-nona-2,4,6,8-tetraenoate. Thereafter, as in Scheme 1, hydrolysis of retinoid esters XIII yields ditritium ring-labeled retinoic acid isomers XVI, such as 3,4-[³H₂]-9-cis retinoic acid ((2E,4E,6Z,SE)-3,4-[³H₂]-3,7-dimethyl-9-(2,6,6-trimethylcyclohex-1-enyl)-nona-2,4,6,8-tetraenoic acid), 3,4-[³H₂]-13-cis retinoic acid, 3,4-[³H₂]-all-trans retinoic acid, and 3,4-[³H₂]-9,13 dicis retinoic acid. Further, a desired ditritium ting-labeled stereoisomer XVI can be selectively crystallized as in Scheme 1 to yield ditritium ring-labeled retinoid stereoisomers XVI, or dideuterium ring-labeled retinoid stereoisomers when retinoate compound XII is selectively reduced with a substantially carder-free deuterium gas.

The synthesis methods of the present invention provide a number of advantages over other labeling methods known in the art. First, the methods allow for the generation of double bonds between ring carbons 2–3 or 3–4, which in turn allow for the selective reduction of such bonds with deuterium or tritium gas to provide dideuterium and/or ditritium ring-labeled retinoids useful for binding and metabolism studies. In particular, the placement of two high activity radiolabels on the retinoid ring increase the radioactivity of such a compound, making them excellent candidates for binding studies. Likewise, placement of two isotopic deuterium labels provides two additional mass units above the non-labeled version of the selected compound, thereby increasing the labeled compounds usefulness in mass spectral metabolism studies. Importantly, the unique placement of the two labels at positions that are not easily oxidized during metabolism make such compounds highly useful to perform a complete range of metabolism studies, through multiple intermediates of the compound as it is oxidatively degraded.

In addition, the preferred methods of the present invention label the compounds of interest at the penultimate stage, which is more economical (limits waste and lost of reagent), and provides high yields of very high activity labeled compounds with essentially pure substitution of deuterium and/or tritium on the ring of the retinoid compounds. However, it will also be appreciated by those skilled in the art that the highly functionalized 1,4-cyclohexadiene-1-carboxaldehyde, and subsequent intermediates, used in the methods of the present invention allows for the labeling with deuterium and/or tritium in the 2 and 3 ring positions at virtually any stage of the process.

In another aspect, the present invention also provides methods of discovering retinoid X receptor (RXR) active and specific ligands utilizing ditritium ring-labeled retinoids (i.e. radiolabeled retinoids) according to the present invention. In particular, a radiolabeled retinoid which is capable of binding to a RXR, such as a ditritium ring-labeled retinoid made by any of the methods of the first aspect of the present invention, can be used in a competition binding assay against the ligand (i.e. the corresponding non-labeled retinoid) to be tested. By comparing the degree to which the radiolabeled retinoid and ligand bind to the RXR relative to the degree of binding of the radiolabeled retinoid to the RXR in the absence of the ligand, the activity of the ligand on the RXR can be determined.

The variations in conducting such competition binding assays are well known to those skilled in the art. For example, one method of conducting such an assay is to first incubate the radiolabeled retinoid in a medium containing an RXR protein until the radiolabeled retinoid is bound to the RXR protein to the point of saturation. Thereafter, the bound RXR protein is washed and incubated with a high concentration (e.g. 200 times) of the ligand (non-labeled retinoid) to be tested. By comparing the quantity of bound radiolabeled retinoid displaced by the ligand the relative activity of the ligand on the RXR, if any, can be determined. Alternatively, when the saturation curve of the radiolabeled retinoid on the RXR is already known, then the radiolabeled retinoid and ligand can be incubated with the RXR at the same time, and the degree of exclusion of the binding of the radiolabeled retinoid to the RXR used to measure the relative activity of the ligand on the RXR, if any.

The RXR proteins used in the competition binding assays of the methods of the present invention will generally be recovered from cell lysates of an appropriate cell culture transfected with a recombinant plasmid capable of expressing the RXR proteins. However, any appropriate means of expressing a sufficient quantity of one or more retinoid X receptors to allow for the conducting of the identification methods of the present invention can be employed. Furthermore, any biologically compatible medium in which the competition binding assays of the present invention can function is considered to be within the scope of the present invention.

To help ensure an accurate measurement of the amount of radiolabeled retinoid that can bind to a particular RXR, it is preferred that the specific binding of the radiolabeled retinoid be determined by titrating the bound radiolabeled retinoid against an excess quantity of the same compound in a nonradioactive form. For example, the radiolabeled retinoid is first incubated with a given RXR to the point of saturated binding. An appropriate binding curve is then generated which shows total binding, both specific binding to the RXR pocket, and nonspecific binding to other associated structures (e.g. lipids). Thereafter, the RXR bound with the radiolabeled retinoid is incubated with a large excess of the non-labeled version of the radiolabeled retinoid (e.g. 200 times or greater concentration). Any radiolabeled retinoid that remains bound, as shown by an appropriate binding curve, is nonspecifically bound. By subtracting the nonspecifically bound protein from the total bound protein, a binding curve can be generated which shows the total specific binding of the radiolabeled retinoid to the RXR. This in turn provides the reference useful for determining the concentration of a tested ligand that displaces the radiolabeled retinoid from an RXR in the methods of the present invention.

In a preferred aspect of the method of the present invention, the radiolabeled retinoid will show activity (e.g. binding) on both retinoid X receptors (RXRs) and retinoic acid receptors (RARs). In such an instance, the radiolabeled retinoid can be used to not only identify compounds that are active on RXRs and RARs, but will also prove useful for identifying ligands that selectively activate one subfamily of retinoid receptors, but not the other. For example, such a radiolabeled retinoid would prove useful for identifying ligands that selectively activate one or more RXR, but do not activate any of the RARs. In fact, such a preferred compound is ditritium ring-labeled 9-cis retinoic acid and its related analogs, such as (2E,4E,6Z,8E)- 4,5-[$^3$H$_2$]-3,7-dimethyl-9-(2,6,6-trimethylcyclohex-1-enyl)-nona-2,4,6,8-tetraenoic acid formed via the methods of the present invention. As can be seen in Table 1 herein, 9-cis retinoid acid is active on all six known retinoid receptors (RAR$\alpha,\beta,\gamma$ and RXR$\alpha,\beta, \gamma$), in contrast to all-trans retinoic acid (ATRA), which is only active on RAR$\alpha,\beta,\gamma$. Thus, 9-cis retinoic acid can be used in the method of the present invention to identify ligands which are specific to any one of the six retinoid receptors, in addition to identifying ligands that are specific to either the RAR or RXR subfamily of receptors.

It will be understood by those skilled in the art that the above methods can be used to yield isotopically stable, ring-labeled 9-cis retinoids that are particularly useful in metabolism studies using a mass spectrometer to locate metabolites of both the isotopically ring-labeled and non-labeled 9-cis retinoids. See e.g., T. A. Baillie et al., J. Clin. Pharmacol., 26:481 (1986) and L. Weidolf and T. R. Covey, *Rapid Comm. Mass. Spectrom.*, 6:192 (1992), the disclosures of which are herein incorporated by reference. For example, a 1:1 mixture of a dideuterium ring-labeled compound (such as (2E,4E,6Z,8E)-4,5-[$^2$H$_2$]-3,7-dimethyl-9-(2, 6,6 -trimethylcyclohex-1-enyl)-nona- 2,4,6,8-tetraenoic acid) and a non-labeled (naturally occurring) compound (such as 9-cis retinoic acid) is administered to an in vitro (e.g., an appropriate cell line) or an in vivo (e.g., an animal model, such as laboratory mice) system, followed by extraction of metabolites from the system (e.g. whole cell lysates or animal bodily fluids). The metabolites may now be identified by their characteristic mass spectral profiles. In particular, such metabolites will exhibit a pair of spectral peaks four mass units apart, which will be visualized in a 1:1 ratio. Importantly, the methods of the present invention yield such ting-labeled 9-cis retinoids with tritium atoms at carbon positions 2 and 3 or 3 and 4, i.e. a positions that show low susceptibility to metabolic oxidation, thereby allowing for completion of metabolic studies throughout the multiple intermediates of the compound as it is oxidatively metabolized.

Furthermore, isotopic ring-labeled 9-cis retinoids according to the present invention can also be used as quantitative standards in mass spectral studies to determine the quantity of non-labeled drug in biological fluids (e.g., blood). See e.g., R. L. Dobson et al., *Anal. Chem.*, 62:1819 (1990), the disclosure of which is herein incorporated by reference. Briefly, a known amount of an isotopic ring-labeled 9-cis retinoids according to the present invention is added to a biological fluid (e.g., a blood sample from a clinical patient) containing an unknown amount of the non-labeled version of the 9-cis retinoid (e.g., 9-cis retinoic acid). Thereafter, the sample spiked with the known amount of isotopic ring-labeled 9-cis retinoid is subjected to mass spectrometry. The resulting mass spectral graph for the sample can then be compared to a standard curve generated in a control sample containing a fixed amount of isotopic ring-labeled 9-cis retinoid and increasing amounts of a non-labeled 9-cis retinoid. A comparison of the peak for the non-labeled compound in the sample to that of the standard curve will give a direct, quantitative read on the amount of non-labeled 9-cis retinoid in the biological sample being tested.

The invention will be further illustrated by reference to the following non-limiting Examples.

EXAMPLE 1

Syntheses of retinoids according to Scheme 1 were performed using both hydrogen, deuterium and tritium gas, thereby yielding non-labeled retinoids (i.e., without an isotopic or radioactive label), and dideuterium and ditritium ring-labeled retinoids. The synthesis is presented with all the necessary physical and spectral properties of the non-labeled retinoids, to provide a means of characterizing the intermediates and deuterium and tritium ring-labeled retinoid products. In the synthesis of retinoids according to Scheme 1, retinoid numbering conventions are used to define the $^1$H-NMR and $^3$H-NMR data.

Synthesis of 2,3-[$^3$H$_2$]9-cis retinoic acid (XI) and precursors per Scheme 1

Ethyl isopropylidene acetoacetate (II where $R^1$, $R^2$, and $R^3$ are methyl) This compound was prepared according to G. Büchi et al., *Helv. Chim. Acta*, 54:1767 (1971), the disclosure of which is herein incorporated by reference. The reaction of ethyl acetoacetate I (where $R^3$ is methyl), acetone and acetic anhydride in the presence of fused zinc chloride proceeded in 36% yield to give the desired compound II: TLC (diethyl ether:petroleum ether 1:4) $R_f$ 0.4; bp. 82°–87° C. at 4.0 mmHg; $^1$H-NMR (CDCl$_3$; 400 MHz) δ (ppm):4.23 (q, J= 7 Hz, 2 H, O—CH$_2$—), 2.3 (s, 3 H, vinyl-CH$_3$), 2.09 (s, 3 H, vinyl-CH$_3$), 1.95 (s, 3 H, C(O)—CH$_3$), 1.3 (t, 3 H, CH$_3$—CH$_2$—O—).

Ethyl 2,6,6-trimethyl-2,4-cyclohexadiene-1-carboxylate (III where $R^1$, $R^2$, and $R^3$ are methyl) A flame-dried 2 L 3-neck roundbottom flask was charged, under a nitrogen atmosphere, with allyltriphenylphosphonium chloride (Aldrich Inc.) (66.86 g, 0.197 tool) and anhydrous diethyl ether (800 mL). The suspension was cooled to 0° C. and n-BuLi in hexanes (126.0 mL of a 1.6M solution, 0.2 mol) was added over a 30 min. period using an addition funnel. The orange colored mixture was stirred at 0° C. for 60 min., then treated with ethyl isopropylidene acetoacetate II (30.5 g, 0.179 mol) in anhydrous diethyl ether (150 mL) over a 15 rain period. The reaction mixture was stirred at room temperature for 60 min. and cold water ( 100 mL) was slowly added. The two phases were separated and the aqueous layer was extracted with diethyl ether (200 mL). The combined organic extract was washed successively with water (100 mL), saturated brine solution (2×50 mL), dried over MgSO$_4$ and concentrated in vacuo to give a semi-solid reddish material which was passed over a short silica gel column (10×8 cm) using a mixture of hexanes:ethyl acetate 4:1. The appropriate fractions were combined, concentrated and the residue distilled [93°–95° C. at 8 Torr] to give 16.75 g of pure ester III: 48% yield; IR (neat) 2964 (CH aliph.), 1738 (C=O), 1446 cm$^{-1}$ (C=C); $^1$H NMR (CDCl$_3$; 400 MHz) δ (ppm): 5.76 (m, 1 H, H$_4$), 5.74 (s, 1 H, H$_5$), 5.35 (d, J=9.6 Hz, 1 H, H$_3$), 4.10 (q, J= 7.0 Hz, 2 H, —CH$_2$—O), 2.74 (s, 1 H, H$_1$), 1.75 (s, 3 H, CH$_3$, ring 2 -position), 1.21 (t, J= 7.0 Hz 3 H, CH$_3$—CH$_2$—O), 1.05 (s, 3 H, gem.—CH$_3$), 1.03 (s, 3 H, gem. CH$_3$); $^{13}$C-NMR (CDCl$_3$; 100 MHz) δ (ppm): 171.9, 134.3, 130.8, 121.3, 120.3, 60.0, 56.7, 34.4, 28.1, 24.4, 22.3, 14.2.

2,6,6-Trimethyl-2,4-cyclohexadiene-1-methanol (Not Shown) A solution of ethyl 2,6,6-trimethyl-2,4-cyclohexadiene-1-carboxylate III (9.09 g, 0.0468 mol) in anhydrous diethyl ether (100 mL) was slowly added to a suspension of LiAlH$_4$ (3.75 g, 0.099 mol) in diethyl ether (200 mL) at 0° C. The mixture was stirred for 4 h and monitored by thin layer chromatography (TLC). Water (4.0 mL) was carefully added, followed by 15% NaOH (4.0 mL) and water (12 mL). The white precipitate was filtered and rinsed with warm EtOAc (100 mL). EtOAc (100 mL) was added and the combined organic layer was washed with water (3×50 mL), brine (3×50 mL), dried (MgSO$_4$) and concentrated. The residue was purified by silica gel chromatography (hexanes:EtOAc 4:1) to give 6.15 g (87% yield) of pure 2,6,6 -trimethyl-2,4-cyclohexadiene-1-methanol; IR (neat) 3340 (—OH), 2958 (CH aliph.), 1467 (C=C), 1442, 1375, 1357, 1049, 1012 cm$^{-1}$;$^1$H-NMR (CDCl$_3$; 400 MHz) δ (ppm): 5.76 (m, 1 H, H$_3$), 5.69 (m, 1 H, H$_2$), 5.36 (d, 9.4 Hz, 1 H, H$_4$), 3.73 (m, 2 H, —CH$_2$OH), 1.85 (s, 3 H, —CH$_3$, ring), 1.77 (t, J=4.1 Hz, 1 H, OH), 1.55 (t, J=5.0 Hz, 1 H, CH ring), 1.14 (s, 3 H, gem CH$_3$), 1.02 (s, 3 H, gem CH$_3$); $^{13}$C-NMR (CDCl$_3$; 100 MHz) δ (ppm): 2 diastereomers: 136.6, 135.2, 135.0, 122.3, 120.7, 120.3, 118.8, 63.1, 61.7, 61.6, 60.3, 52.2, 50.9, 33.7, 28.1, 26.9, 25.4, 24.1, 22.5, 21.2.

2,6,6-Trimethyl-2,4-cyclohexadiene, 1-carboxaldehyde (IV where $R^1$, $R^2$, and $R^3$ are methyl) A flame-dried 500 mL round bottom flask was charged, under a nitrogen atmosphere, with anhydrous tetrahydrofuran (THF) (150 mL) and oxalyl chloride (4.25 mL, 0.049 mol), then cooled to −78° C. (acetone-dry ice bath). Dimethylsulfoxide (DMSO) (6.95 mL, 0.097 mol) was slowly added, the mixture warmed to −35° C. for 3 min. and cooled again to −78° C. A solution of 2,2,6-trimethyl- 2,4-cyclohexadiene-1-methanol from the previous step (5.50 g, 0.0362 mol) in anhydrous THF (50 mL) was added dropwise. The mixture was stirred at −78° C. for an additional 20 min. and warmed to −35° C. for 30 min. The turbid solution was then cooled to −78° C., treated with triethylamine (14.65 mL, 0.105 mol) and allowed to warm to room temperature. A saturated solution of ammonium chloride (50 mL) was added, followed by EtOAc (100 mL). The organic layer was washed with water (3×50 mL), brine (50 mL) and dried over MgSO$_4$ and concentrated. The residue was purified by silica gel chromatography (Hexanes:EtOAc 10:1 ) to give 5.31 g of the aldehyde IV (96% yield). IR (neat) 2960 CH), 1716 (C=O) cm$^{-1}$; $^1$H-NMR (CDCl$_3$; 400 MHz) δ (ppm): 9.29

(d, J= 5.5 Hz, 1 H, CHO), 5.9 (m, 1 H, vinyl CH), 5.75 (m, 1 H, vinyl —CH), 5.43 (d, J=9.4 Hz, 1 H, vinyl CH), 2.28 (d, J=5.3 Hz, 1 H, C$\underline{H}$—CHO), 1.71 (s, 3 H, CH$_3$ ring), 1.06 (s, 3 H, CH$_3$ ring), 1.00 s, 3 H, CH$_3$ ring); $^{13}$C-NMR (CDCl$_3$; 100 MHz) δ (ppm): 2 diastereomers: 200.3, 134.6, 129.2, 122.3, 122.1, 63.9, 33.6, 31.8, 29.3, 26.4, 25.6, 22.6, 22.1.

2,6,6-Trimethyl-1,4-cyclohexadiene-1-carboxaldehyde (V where R$^1$, R$^2$, and R$^3$ are methyl) To a solution of 2,6,6-trimethyl-2,4-cyclohexadiene-1-carboxaldehyde IV (3.70 g, 24.8 mmol) in anhydrous dichloromethane (25 mL) was added 1,8-diazabicyclo[5.4.0]undec7-ene (DBU) (0.150 mL, 0.98 mmol) in three (3) portions over 30 min. while the mixture was stirred at 0° C. The solution was warmed to room temperature and the progress of the reaction was monitored by TLC (hexanes:EtOAc 9:1). The two isomeric aldehydes are separable on TLC (R$_f$ SM 0.85; R$_f$ product 0.75). After 60 min., the reaction was complete. A saturated solution of ammonium chloride (20 mL) was added, followed by dichloromethane (100 mL). The organic layer was separated and washed with a saturated solution of brine, dried over MgSO$_4$ and concentrated. The residue was purified by silica gel chromatography (SGC) using a mixture of hexanes:EtOAc 15:1 as eluent to give 3.1 g of the desired aldehyde V (83% yield). IR (neat) 2960 CH), 1716 (C=O) cm$^{-1}$; $^1$H-NMR (CDCl$_3$; 400 MHz) δ (ppm): 10.18 (s, 1 H, CHO), 5.44, (m, 2 H, vinyl—CH), 2.81 (s, 2 H, —CH$_2$—), 2.12 (s, 3 H, CH$_3$ ring), 1.25 (s, 6 H, 2×CH$_3$ ring); $^{13}$C-NMR (CDCl$_3$; 100 MHz) δ (ppm): 191.8, 152.1,138.4, 117.4, 35.6, 34.2, 28.1, 22.6, 18.47, 14.0.

5,6-Dihydro-4-methyl-6-(2,6,6-trimethyl-1,4-cyclohexadiene-1-yl)-2H-pyran-2-one (VI where R$^1$, R$^2$, R$^3$ and R$^4$ are methyl) A solution of lithium diisopropylamide (LDA) was prepared as follows: A flame-dried 500 mL round bottom flask was charged with tetrahydrofuran (THF) (100 mL) and anhydrous diisopropylamine (distilled over CaH and kept over KOH under a nitrogen atmosphere) (2.65 mL, 19 mmol), then cooled to −20° C. A solution of n-BuLi in hexanes (7.35 mL of a 2.35 M solution; 18.2 mmol) was added over a 10 min. period. The solution was stirred at −20° C. for 15 min, then cooled to −78° C. A solution of ethyl dimethylacrylate (Aldrich Inc.) (1.92 g, 15 mmol) in THF (5.0 mL) was added slowly at such a rate that the internal temperature did not exceed −73° C. The mixture was stirred at −78° C. for 30 rain followed by dropwise addition of a precooled solution (−78° C.) of 2,2,6-trimethyl-1,4-cyclohexadiene-1-carboxaldehyde V (2.25 g, 15 mmol) in 25 mL of THF. When the addition was complete, the reaction mixture was warmed immediately to 0° C. and quenched with a saturated sodium bicarbonate solution (3.0 mL). The mixture was stirred at room temperature for 60 min., water (10 mL) was added and the aqueous layer extracted with EtOAc (2×50 mL). The organic layer was washed with brine (2×10 mL), dried over MgSO$_4$ and concentrated. The residue was purified by SGL using a mixture of hexanes:EtOAc 5:1 as eluent to give 1.53 g of the desired lactone VI (44% yield): mp 77°–79° C.; IR (neat) 2958 (CH aliph.), 1720 (C=O), 1383 (C=C), 1294, 1251 cm$^{-1}$; $^1$H-NMR (CDCl$_3$; 400 MHz) δ (ppm): single diastereomer: 5.82 (s, 1 H, CH—C(O)O—), 5.50 (m, 1 H, vinyl—CH), 5.39 (m, 1 H, vinyl—CH), 5.01 (dd, J=13.3, 4.4 Hz, 1 H, —CH—O—C(O)) 2.84 (m, 1H, —CH—CH—O—, syn), 2.60 (m, 2 H, C=CH—CH$_2$—C=C), 2.12 (dd, J=16.3, 4.4 Hz, 1 H, —CH—CH—O—, anti), 1.97 (s, 3 H, CH$_3$ ring), 1.79 (s, 3 H, CH$_3$ ring) 1.13 (s, 3 H, CH$_3$ ring), 1.01 (s, 3 H, CH$_3$ ring); $^{13}$C-NMR (CDCl$_3$; 100 MHz) δ (ppm): 165.8, 157.6, 135.8, 132.5, 131.6, 119.9, 116.2, 75.3, 35.9, 35.2, 34.18, 28.9, 28.5, 22.8, 20.5.

5,6-Dihydro-4-methyl-6-(2,6,6-trimethyl-1,4-cyclohexadiene-1-yl)-2H-pyran-2-ol (Structure not shown) To a cooled (−78° C.) solution of 5,6-dihydro-4-methyl-6-(2,6,6-trimethyl-1,4-cyclohexadiene-1-yl)-2H pyran-2-one VI (223 mg, 0.96 mmol) in THF (10.0 mL) was slowly added a solution of diisobutylaluminum hydride in toluene (1.0 mL of a 1.0M solution). After 15 min., TLC (Hexanes:EtOAc 4:1) monitoring showed that the reaction was complete. A saturated solution of Rochelle salt (4.0 mL) was added at −78° C., and the mixture was allowed to warm to room temperature. EtOAc (20 mL) was added and the layers were separated. The aqueous layer was thoroughly extracted with EtOAc (3×10 mL) and the combined organic layers were washed with brine (20 mL) and concentrated to give 220 mg of virtually pure (by TLC) desired lactol; 98% yield. The compound was obtained as a white solid (mp.: 146°–148° C.) and was shown to be a single diastereomer by $^1$HNMR. However, both in solution in chloroform and upon silica gel chromatography, it isomerizes to an anomeric mixture (~55:45); IR (KBr) 3387, 2935, 1688 (weak) cm$^{-1}$; $^1$H-NMR (CDCl$_3$; 400 MHz) δ: 2 diastereomers: 5.52 (m, 2×2 H), 5.39 (s 2×1 H), 5.35 (m, 2×1 H), 4.71 (dd, J= 11.2, 4.4 Hz, 1 H), 4.3 (dd, J=13, 4.4 Hz, 1 H), 3.0 (d, J=11 Hz, 1 H), 2.88 (d, J= 4.2 Hz, 1 H) 2.7–2.45 (m 2×4 H), 1.87 (s 3 H), 1.81 (s, 3 H), 1.73, (s, 3 H), 1.13 (s, 3 H), 1.1 (s, 3 H), 1.01 (s, 3 H), 0.99 (s 3 H); $^{13}$C NMR (CDCl$_3$; 100 MHz) δ (ppm): Major: 137.8, 136.2, 134.9, 129.9, 119.9, 119.8, 89.7, 65.2, 36.4, 35.4, 34.1, 28.8, 28.4, 22.7, 20.2; Minor: 137.6, 135.9, 134.5, 129.8, 122.7, 116.3, 93.0, 70.73, 35.9, 35.4, 34.0, 28.8, 28.4, 22.5, 19.8.

(2Z,4E)-3-Methyl-5-(2,6,6-trimethylcyclohex-1,4-dienyl)-2,4-pentadienenal (VII where R$^1$, R$^2$, R$^3$ and R$^4$ are methyl) A solution of 5,6-dihydro-4-methyl-6-(2,6,6-trimethyl-1,4-cyclohexadiene-1-yl)-2H-pyran-2-ol (220 rag, 0.94 mmol) used directly from the last step, in 1,2-dichloroethane (5.0 mL) was added to 10% HCL (5.0 mL), and the biphasic system was heated to 55° C. with vigorous stirring. The reaction was monitored carefully by TLC and was complete after 60 min. The mixture was cooled to room temperature and neutralized with a saturated NaHCO$_3$ solution. The layers were separated and the aqueous phase extracted with dichloromethane (2×10 mL). The combined organic extract was washed with water (2×5 mL) and brine (10 mL), dried over MgSO$_4$ and concentrated. The residue was purified on a short silica gel column to give 174 mg (87% yield) of the desired aldehyde VII as a yellow oil: IR (neat) 2958, 2928, 2866, 1668 (C=O), 1614 (C=C); $^1$H-NMR (CDCl$_3$; 400 MHz) δ (ppm) 10.16 (d, J=8.0 Hz, CHO), 7.16 (d , J=16.0 Hz, vinyl—CH, trans), 6.63 (d , J=16.0 Hz, vinyl—CH, trans), 5.88 (d, J=8.0 Hz, 1H, CH—CHO), 5.58 (m, 1 H, H$_3$), 5.49 (m, 1 H, H$_4$), 2.69 (s, 2 H, =CH—CH$_2$—C(CH$_3$)=), 2.14 (s, 3 H, —C—(CH$_3$)=CH—CHO, cis), 1.80 (s, 3 H, CH$_3$, ring), 1.11 (s, 6 H, gem-2×CH$_3$); $^{13}$C NMR (CDCl$_3$; 100 MHz) d (ppm): 201.0, 190.0, 154.8, 136.6, 135.6, 135.5, 129.3, 128.3, 128.0, 120.1, 35.7, 33.5, 29.5, 21.1, 21.0.

Ethyl (2E,4E,6Z,8E)-3,7-dimethyl-9-(2,6,6-trimethylcyclohex-1,4-dienyl)-nona- 2,4,6,8-tetraenoate (VIII where R$^1$, R$^2$, R$^3$, R$^4$ and R$^5$ are methyl, R$^6$ is ethyl) A solution of diethyl 3 -ethoxycarbonyl-2-methylprop-2-enylphosphonate (354 mg, 1.34 mmol) in anhydrous THF (5.0 mL) was cooled to 0° C., followed by addition of anhydrous DMPU (0.5 mL) and n-BuLi in hexanes (0.56 mL of a 2.35M solution, 1.33 mmol). The mixture was stirred at 0 ° C. for 20 min, then cooled to −78° C. A solution of (2Z,4E)-3-methyl-5 -(2,6,6-trimethylcyclohex-1,4-dienyl)-

2,4-pentadienenal VII (241 rag, 1.115 mmol) in THF (3.0 mL) was slowly added, and the reaction mixture was stirred at −78° C. for an additional 60 min. The mixture was warmed to 0° C., and the reaction went to completion as monitored by TLC. A saturated solution of ammonium chloride (5 mL) was added, and the mixture extracted using EtOAc (3×10 mL). The organic layer was washed with water (2×5 mL), brine (10 mL), dried over $MgSO_4$ and concentrated. The residue was purified on a short silica gel column to give 296 mg (78% yield) of the desired ester VIII in a ~15:1 ratio of 13-trans:13-cis isomers: IR (neat) 2928, 1709 $cm^{-1}$; $^1$H-NMR ($CDCl_3$; 400 MHz) δ (ppm): 7.08 (dd, J=15, 11.3 Hz, 1 H), 6.65 (d, J=16 Hz, 1 H), 6.29 (d, J=15 Hz, 1 H), 6.23 (d, J=15 Hz, 1 H), 6.06 (d, J= 11.3 Hz, 1 H), 5.6 (m, 1 H), 5.52 (m, 1 H), 4.17 (d, J=7 Hz, 2 H), 2.7 (s, 2 H), 2.33 (s, 3 H), 2.03 (s 3 H), 1.82 (s, 3 H) 1.29 (t, J=7 Hz, 3 H), 1.1 (s, 6 H).

Ethyl (2E,4E,6Z,8E)-4,5-[$^3H_2$]-3,7-dimethyl-9-(2,6,6-trimethylcyclohex- 1-enyl)-nona-2,4,6,8-tetraenoate (IX where $R^1$, $R^2$, $R^3$, $R^4$ and $R^5$ are methyl, $R^6$ is ethyl) A suspension of Wilkinson's catalyst (180 mg, 0.195 mmol) in 2 mL of benzene was degassed under $N_2$-freeze-thaw conditions, followed by addition of tritium gas (at 750 mm Hg). After stirring for 2 hrs under a tritium atmosphere the mixture turned to a homogeneous yellow-orange color. To this stirred mixture was added 30 mg (0.092 mmol) of the ester IX in 1 mL of benzene. The solution was stirred for 2 hours, followed by addition of hexane and filtration through silica gel. The product was concentrated and used directly in the next step.

(2E,4E,6Z,8E)-4,5-[$^3H_2$]-3,7-Dimethyl-9-(2,6,6-trimethylcyclohex-1 -enyl)-nona- 2,4,6,8-tetraenoic acid (XI where $R^1$, $R^2$, $R^3$, $R^4$ and $R^5$ are methyl, $R^7$ is hydrogen) The crude product IX was dissolved in 5 mL of MeOH, followed by addition of 2 mL of 5N aqueous KOH. The reaction was heated to reflux for 30 min., cooled to 0° C., and acidified with 1N aqueous HCl. The product was extracted with EtOAc (3×5 mL), and the combined extract was washed with brine, dried over $MgSO_4$ and concentrated. HPLC purification ($C_{18}$-ODS, 65% $CH_3CN$-35% $H_2O$-0.5% AcOH) gave 3.2 Curies of pure [$^3H_2$]-9-cis-retinoic acid XI, specific activity >60 Ci/mmol. TLC (20% EtOAc-hexane) $R_f$ 0.26; UV(MeOH) $\lambda_{max}$ 343 nm; $^1$H-NMR ($CD_3OD$) δ 1.05 (s, 1-($CH_3$)$_2$), 1.48 (t, J=3, 9 Hz, 2-$CH_2$), 1.64 (dtt, J=11, 6, 3 Hz, 3-$CH_2$), 1.71 (s, 18-$CH_3$), 1.98 (s, 19-$CH_3$), 2.04 (t, J=6 Hz, 4-$CH_2$), 2.29 (s, 20-$CH_3$), 5.79 (s, 14-CH), 6.11 (d, J= 12 Hz, 10-CH), 6.30 (brd, J=16 Hz, 7-CH+12-CH), 6.70 (d, J=17 Hz, 8-CH), 7.11 (dd, J=12 Hz, 16 Hz, 11-CH); 3H-NMR ($CD_3OD$) δ 1.48 (d, J=3 Hz, 2-$C^3$ H), 1.64 (d, J=3 Hz, 3-$C^3$H).

EXAMPLE 2

In the synthesis of retinoids according to Scheme 2, retinoid numbering conventions are used to define the $^1$H-NMR and $^3$H-NMR data.

Preparation of 3,4-[$^3H_2$]9-cis retinoic acid (X1V) per Scheme 2

Ethyl (2E,4E,6Z,8E)-3,4-[$^3H_2$]-3,7-dimethyl-9-(2,6,6 -trimethylcyclohex-1-enyl)-nona- 2,4,6,8-tetraenoate (XIII where $R^1$, $R^2$, $R^3$, $R^4$ and $R^5$ are methyl, $R^6$ is ethyl) A suspension of Wilkinson's catalyst (90 mg, 0.097 mmol) in 2 mL of benzene was degassed under $N_2$-freeze-thaw conditions, followed by addition of tritium gas (at 750 mm Hg). After stirring for 2 hrs under a tritium atmosphere the mixture turned to a homogeneous yellow-orange color. To this stirred mixture was added 30 mg (0.092 mmol) of the ester XII (synthesized as previously described) in 1 mL of benzene. The solution was stirred for 2 hours, followed by addition of hexane and filtration through silica gel. The product XIII was concentrated and used directly in the next step.

(2E,4E,6Z,8E)-3,4-[$^3H_2$]-3,7-Dimethyl-9-(2,6,6-trimethylcyclohex- 1-enyl)-nona- 2,4,6,8-tetraenoic acid (XIV where $R^1$, $R^2$, $R^3$, $R^4$ and $R^5$ are methyl, $R^7$ is hydrogen) The crude product XIII was dissolved in 5 mL of MeOH, followed by addition of 2 mL of 5N aqueous KOH. The reaction was heated to reflux for 30 min., cooled to 0° C., then acidified with 1N aqueous HCl. The product was extracted with EtOAc (3×5 mL), and the combined extract was washed with brine, dried over $MgSO_4$ and concentrated. HPLC purification ($C_{18}$-ODS, 65% $CH_3CN$—35% $H_2O$—0.5% AcOH) gave 3.2 Curies of pure [$^3H_2$]-9-cis-retinoic acid XIV, specific activity > 60 Ci/mmol. TLC (20% EtOAc-hexane) $R_f$ 0.26; UV(MeOH) $\lambda_{max}$ 343 nm; $^1$H-NMR ($CD_3OD$) δ 1.05 (s, 1-($CH_3$)$_2$), 1.48 (t, J=3, 9 Hz, 2-$CH_2$), 1.63 (dtt, J=11, 6, 3 Hz, 3-$CH_2$), 1.71 (s, 18-$CH_3$), 1.98 (s, 19-$CH_3$), 2.03 (t, J=6 Hz, 4-$CH_2$), 2.29 (s, 20-$CH_3$), 5.79 (s, 14-CH), 6.11 (d, J= 12 Hz, 10-CH), 6.30 (brd, J=16 Hz, 7-CH+12-CH), 6.70 (d, J=17 Hz, 8-CH), 7.11 (dd, J=12 Hz, 16 Hz, 11-CH); $^3$H-NMR ($CD_3OD$) δ 1.63 (d, J=6 Hz, 3-$C^3$H), 2.03 (d, J=6 Hz, 4-$C^3$H).

EXAMPLE 3

For binding studies, retinoids receptors were used employing a baculovirus expression system. The methods concerning growth, purification, and assays of recombinant viruses followed the protocol outlined by Summers, M.D., and Smith, G. E., *A Manual of Methods for Baculovirus Vectors and Insect Cell Culture Procedures*, Texas Agric. Exp. Stat. Bull., No. 155 (1987). The recombinant plasmids were cotransfected into SF21 cells with wild-type AcNPV DNA, See U.S. Pat. No. 5,071,773, and the recombinant viruses were plaque purified. For the mock (control) extracts, wild-type AcNPV-infected cells were used.

For ligand binding assays, the baculovirus-infected cells were disrupted by Dounce homogenization (Kontes Co., Vineland, N.J.) in 10 nM Tris (pH 7.6), 5 mM dithiothreitol (DTT), 2 mM EDTA 0.5% CHAPS, and 1 mM phenylmethyisulfonyl fluoride. The KCl concentration was adjusted to 0.4M after cell lysis. The cell lysates were centrifuged for 1 hr at 4° C., 100,000×g, and the supernatant was recovered as a high-salt, whole cell extract. For the saturation binding analysis, cell extracts (50 microgram protein) were incubated at 0° C. for 2.0 hr with a ditritium ring-labeled retinoid in the presence or absence of 200-fold excess unlabeled ligand. Specific ligand binding to receptor was determined by a hydroxyapatite binding assay according to the protocol of Wecksler, W. R., and Norman, A. W., *Anal. Biochem.*, 92:314–323 (1979).

Figure 1:
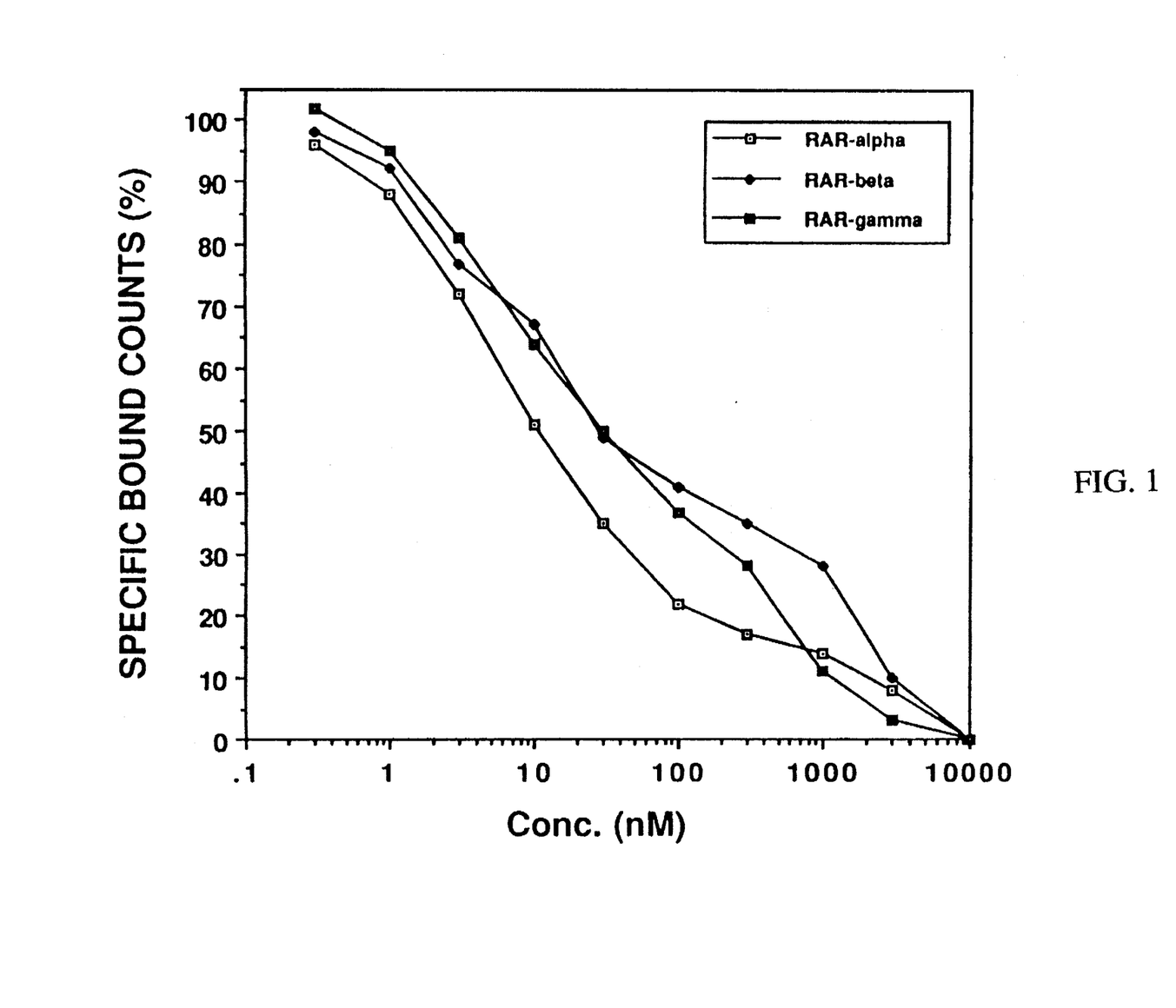
FIG. 1 is a graph showing the total specific binding of ditritium ring-labeled 9-cis retinoic acid (2,3-[$^3H_2$]9 cis retinoic acid) to retinoid acid receptor alpha— RAR$\alpha$(■), beta—RAR$\beta$(♦) and gamma—RAR$\gamma$(□) at increasing concentrations of 9-cis retinoic acid.
Figure 2:
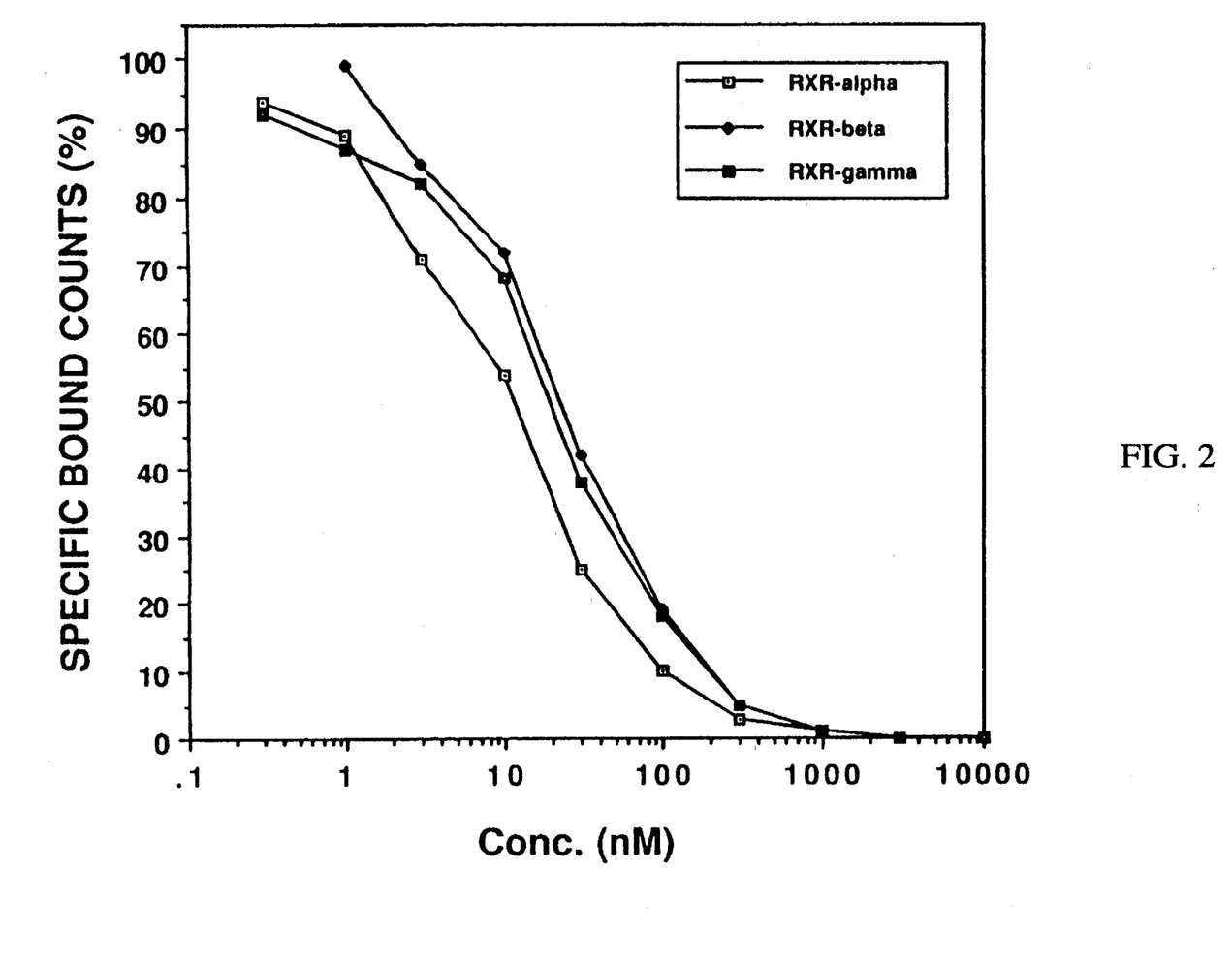
FIG. 2 is a graph showing the total specific binding of ditritium ring-labeled 9-cis retinoic acid (2,3-[$^3H_2$]9 cis retinoic acid) to X receptor alpha— RXR$\alpha$(■), beta— RXR$\beta$(♦) and gamma—RXR$\gamma$(□) at increasing concentrations of 9-cis retinoic acid.

To characterize the binding of 9-cis RA to baculovirus-derived RARs and RXRs, saturation binding analysis were performed using ditritium ting-labeled 9-cis retinoic acid (2,3-[$^3H_2$]9 cis retinoic acid). A typical specific binding curve for 9-cis retinoic acid binding to RARα, RARβ and RARγ is shown in FIG. 1. A comparable specific binding curve for 9-cis retinoic acid binding to RXRα, RXRβ and RXRγ is shown in FIG. 2. In these curves, non-specific binding of any ting-labeled compounds have already been factored out of the overall binding, to yield the specific binding curves shown in FIGS. 1 and 2. Further, Scatchard analysis of the binding of 2,3-[$^3$H$_2$] 9 cis retinoic acid and ATRA to RARα,β,γ and RXRα,β,γ was performed to give the dissociation constants shown in Table 1 below. The data shows that 9-cis-retinoic acid effectively binds to all six receptors whereas ATRA only binds to the RARs. We conclude that 9-cis retinoic acid binds to the RARs and RXRs with high affinity in a saturable and specific manner.

TABLE 1

Mean dissociation constants in Kd (nM) (and standard deviation) for RAR and RXR retinoid receptors with all-trans retinoic acid (ATRA) and 9-cis retinoic acid (9-cis RA).

| Retinoid | RARα | RARβ | RARγ | RXRα | RXRβ | RXRγ |
|---|---|---|---|---|---|---|
| ATRA Mean | 0.45 | 0.37 | 0.22 | — | — | — |
| s.d. | 0.13 | 0.13 | 0.11 | — | — | — |
| 9-cis RA Mean | 0.32 | 0.20 | 0.78 | 1.38 | 2.11 | 1.94 |
| s.d. | 0.07 | 0.09 | 0.14 | 0.37 | 0.75 | 0.76 |

While in accordance with the patent statutes, description of the preferred embodiments and processing conditions have been provided, the scope of the invention is not to be limited thereto or thereby. Various modifications and alterations of the present invention will be apparent to those skilled in the art without departing from the scope and spirit of the present invention.

Consequently, for an understanding of the scope of the present invention, reference is made to the following claims.

What is claimed is:

1. A ring-labeled retinoid of the general formula:

OR wherein R$^1$, R$^2$, R$^3$, R$^4$ and R$^5$ each can independently represent hydrogen or a lower straight chain or branched alkyl, aryl, heteroaryl or aralkyl having 1–12 carbon atoms; R$^7$ represents hydrogen or a pharmaceutically acceptable salt, n=2 or 3; and 9–10, 11–12 and 13–14 olefin bonds are in either the trans or cis configuration.

2. The retinoid of claim 1, wherein R$^1$, R$^2$, R$^3$, R$^4$ and R$^5$ each comprise methyl.

3. The retinoid of claim 1, wherein the 9–10 olefin bond is in the cis configuration.

4. The retinoid of claim 3, wherein the 11–12 and 13–14 olefin bonds are in the trans configuration.

5. The retinoid of claim 1, wherein n=3.

6. The retinoid of claim 5, wherein the ring-labeled retinoid displays a specific activity of at least 15 Curies per millimole.

7. The retinoid of claim 5, wherein the ring-labeled retinoid displays a specific activity of at least 25 Curies per millimole.

8. The retinoid of claim 1, wherein the ring-labeled retinoid comprises (2E,4E,6Z,8E)-3,4-[$^3$H$_2$]-3,7-dimethyl-9-(2,6,6-trimethylcyclohex-1-enyl)-nona-2,4,6,8-tetraenoic acid or (2E,4E,6Z,8E)-4,5-[$^3$H$_2$]-3,7-dimethyl-9-(2,6,6-trimethylcyclohex-1-enyl)-nona-2,4,6,8-tetraenoic acid.

9. A ring-labeled retinoid selected from the group consisting of ethyl (2E,4E,6Z,8E)-3,4-[$^3$H$_2$]-3,7-dimethyl-9-(2,6,6-trimethylcyclohex-1-enyl)-nona-2,4,6,8-tetraenoate, ethyl (2E,4E,6Z,8E)-4,5-[$^3$H$_2$]-3,7-dimethyl-9-(2,6,6-trimethylcyclohex-1-enyl)-nona-2,4,6,8-tetraenoate, (2E,4E,6Z,8E)-4,5-[$^3$H$_2$]-3,7-dimethyl-9-(2,6,6-trimethylcyclohex-1-enyl)-nona-2,4,6,8-tetraenoic acid, (2E,4E,6Z,8E)-4,5-[$^3$H$_2$]-3,7-dimethyl-9-(2,6,6-trimethylcyclohex-1-enyl)-nona-2,4,6,8-tetraenoic acid, ethyl (2E,4E,6Z,8E)-3,4-[ (2E,4E,6Z,8E)-4,5-[$^3$H$_2$]-3,7-dimethyl-9-(2,6,6-trimethylcyclohex-1-enyl)-nona-2,4,6,8-tetraenoate, ethyl (2E,4E,6Z,8E)-3,4-[$^2$H$_2$]-3,7-dimethyl-9-(2,6,6-trimethylcyclohex-1-enyl)-nona-2,4,6,8-tetraenoate, (2E,4E,6Z,8E)-3,4-[$^3$H$_2$]-3,7-dimethyl-9-(2,6,6-trimethylcyclohex-1-enyl)-nona-2,4,6,8-tetraenoic acid, and (2E,4E,6Z,8E)-3,4-[$^2$H$_2$]-3,7-dimethyl-9-(2,6,6-trimethylcyclohex-1-enyl)-nona-2,4,6,8-tetraenoic acid.

\* \* \* \* \*